(12) United States Patent
Jayaram

(10) Patent No.: US 7,137,392 B1
(45) Date of Patent: Nov. 21, 2006

(54) BED SORE PREVENTION ASSEMBLY

(76) Inventor: Bangalore N. Jayaram, 2800 Lake Shore Dr., Unit 817, Chicago, IL (US) 60657

( * ) Notice: Subject to any disclaimer, the term of this patent is extended or adjusted under 35 U.S.C. 154(b) by 69 days.

(21) Appl. No.: 10/929,144

(22) Filed: Aug. 30, 2004

(51) Int. Cl.
*A61F 13/00* (2006.01)
(52) U.S. Cl. .......................... 128/846; 2/465
(58) Field of Classification Search ............ 128/846; 2/465, 46, 47, 48, 108, 69, 69.5, 456, 85, 2/82, 236
See application file for complete search history.

(56) References Cited

U.S. PATENT DOCUMENTS

| | | | |
|---|---|---|---|
| 1,376,783 A | 5/1921 | Schoen | |
| D123,956 S | 10/1940 | De Ware | |
| 3,020,910 A | 2/1962 | Ward | |
| 3,937,218 A | 2/1976 | Gaylord, Jr. | |
| 4,067,330 A | 1/1978 | Roache | |
| 4,701,170 A | 10/1987 | Wilson et al. | |
| 4,807,301 A * | 2/1989 | Ferber | 2/465 |
| 5,157,789 A | 10/1992 | Klass | |

\* cited by examiner

*Primary Examiner*—Henry Bennett
*Assistant Examiner*—Camtu Nguyen

(57) ABSTRACT

A bed sore prevention assembly includes a flexible panel that has a first side, a second side, a top edge, a bottom edge, a first lateral edge and a second lateral edge. A plurality of cushion members is attached to the first side of the panel. A fastening member selectively secures the panel in a loop formation. The fastening member includes a first engaging member that is attached to the first side of the panel and positioned adjacent to the first lateral edge and a second engaging member that is attached to the second side of the panel and positioned adjacent to the second lateral edge of the panel. The first engaging member is adapted for removably coupling with the second engaging member to define a body wrap.

8 Claims, 3 Drawing Sheets

BED SORE PREVENTION ASSEMBLY

BACKGROUND OF THE INVENTION

1. Field of the Invention

The present invention relates to bed sore treating and preventing devices and more particularly pertains to a new bed sore treating and preventing device that may worn by a bedridden person for aiding in the prevention of bedsores.

2. Description of the Prior Art

The use of bed sore treating and preventing devices is known in the prior art. U.S. Pat. No. 3,937,218 describes a pad having a unique shape for being worn on a heel or elbow of a patient for the prevention of bedsores, or decubitus ulcers, to those areas. U.S. Pat. No. 4,067,330 describes a bandage assembly for the treating of bedsores. A similar device is U.S. Pat. No. 4,701,170 describes a form fitting disposable garment which. Another analogous device is found in U.S. Pat. No. 5,157,789 that describes a hip garment adapted for being worn about the body and which includes padding for the prevention of injury should a patient wearing the garment accidentally fall onto their hip.

While these devices fulfill their respective, particular objectives and requirements, the need remains for a device that has a structure for preventing the acquisition of bedsores in areas of the body where the bones create distinct pressure points for a person lying in a bed. In particular, a device is need that may be worn as a body wrap for protecting the hipbone and tailbone areas. Such a garment will reduce the chances of bedsores developing in those areas.

SUMMARY OF THE INVENTION

The present invention meets the needs presented above by generally comprising a flexible panel that has a first side, a second side, a top edge, a bottom edge, a first lateral edge and a second lateral edge. A plurality of cushion members is attached to the first side of the panel. A fastening member selectively secures the panel in a loop formation. The fastening member includes a first engaging member that is attached to the first side of the panel and positioned adjacent to the first lateral edge and a second engaging member that is attached to the second side of the panel and positioned adjacent to the second lateral edge of the panel. The first engaging member is adapted for removably coupling with the second engaging member to define a body wrap.

There has thus been outlined, rather broadly, the more important features of the invention in order that the detailed description thereof that follows may be better understood, and in order that the present contribution to the art may be better appreciated. There are additional features of the invention that will be described hereinafter and which will form the subject matter of the claims appended hereto.

The objects of the invention, along with the various features of novelty which characterize the invention, are pointed out with particularity in the claims annexed to and forming a part of this disclosure.

BRIEF DESCRIPTION OF THE DRAWINGS

The invention will be better understood and objects other than those set forth above will become apparent when consideration is given to the following detailed description thereof. Such description makes reference to the annexed drawings wherein.

DESCRIPTION OF THE PREFERRED EMBODIMENT

Figure 1:
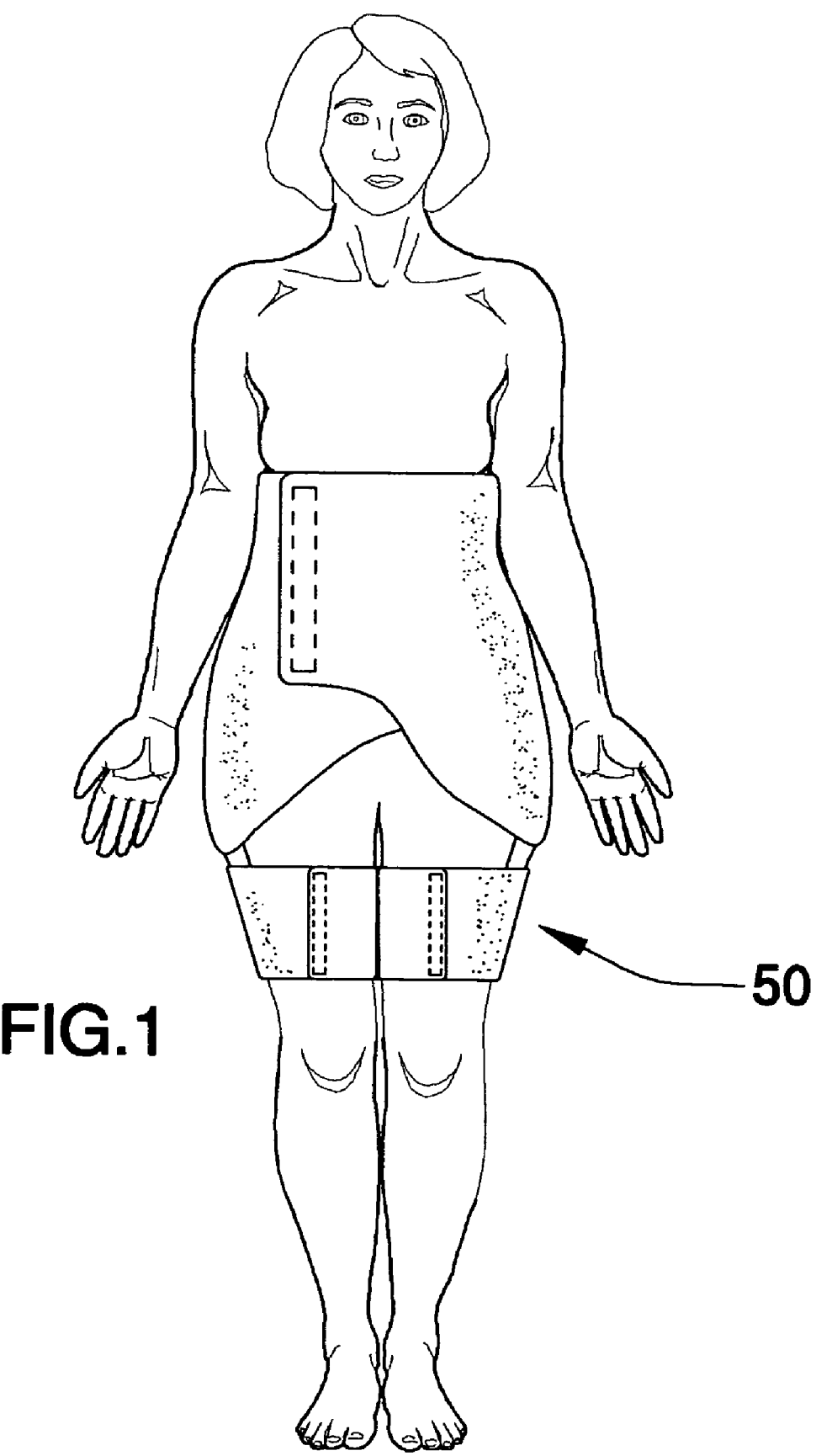
FIG. 1 is a front in-use view of a bed sore prevention assembly according to the present invention.
Figure 2:
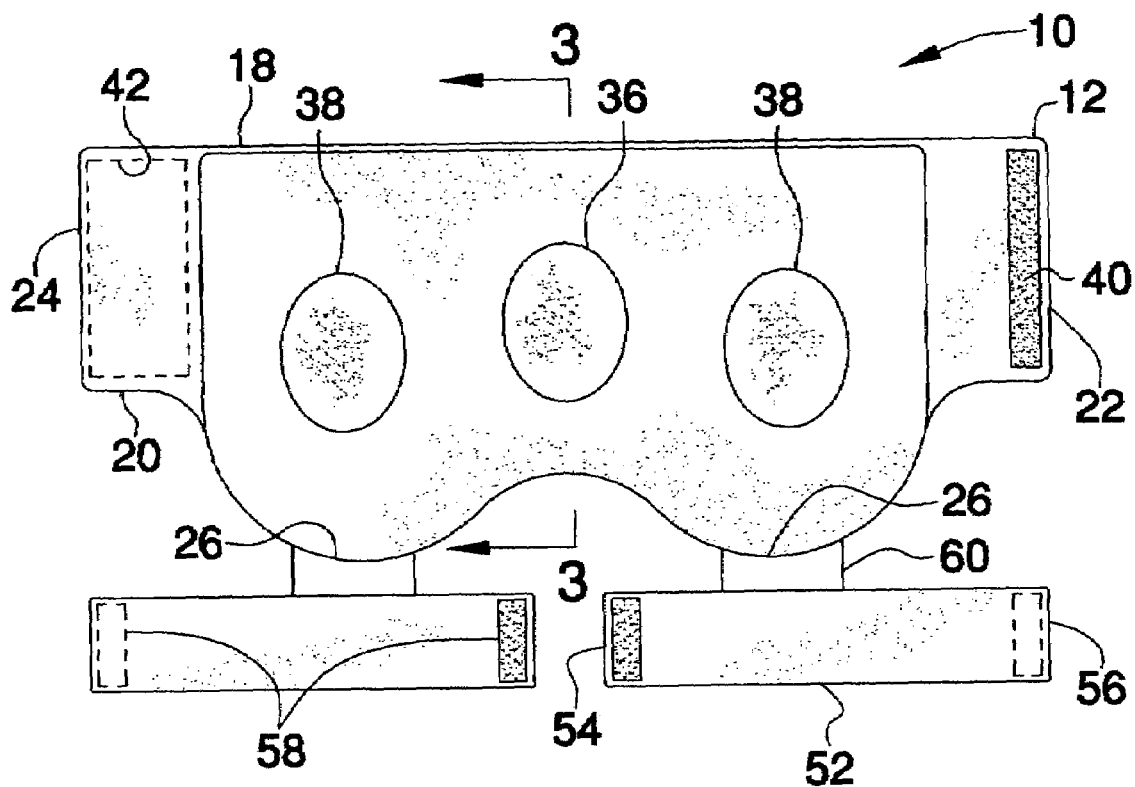
FIG. 2 is a front view of the present invention.
Figure 3:
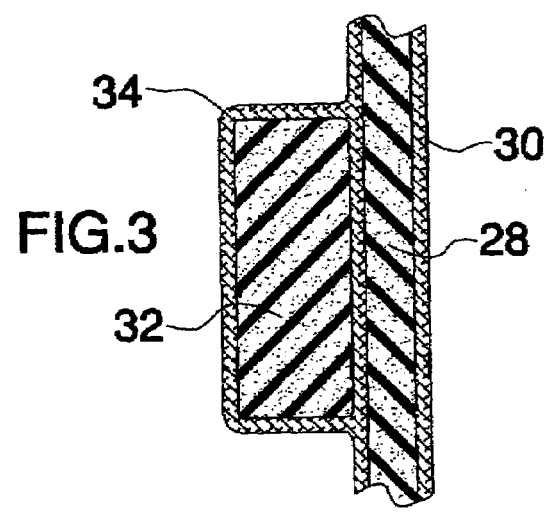
FIG. 3 is a cross-sectional view taken along line 3—3 of FIG. 2 of the present invention.
Figure 4:
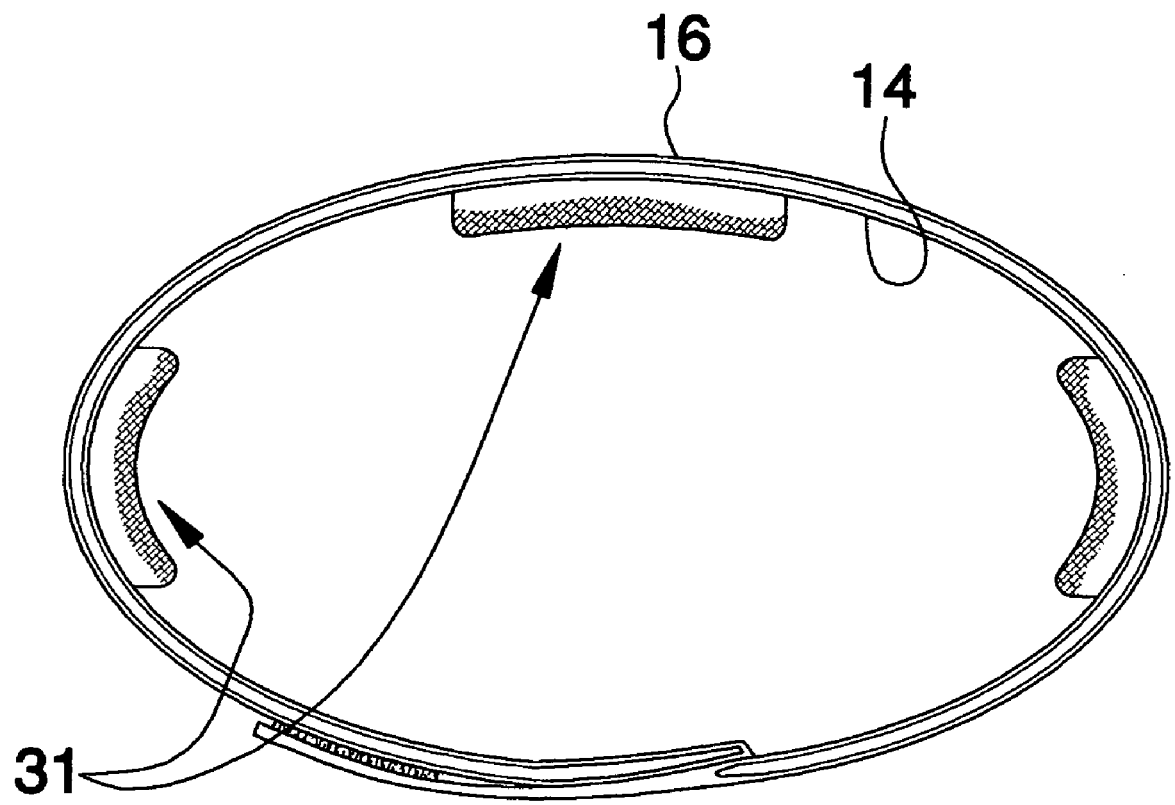
FIG. 4 is a top view of the panel of the present invention.

With reference now to the drawings, and in particular to FIGS. 1 through 4 thereof, a new bed sore treating and preventing device embodying the principles and concepts of the present invention and generally designated by the reference numeral 10 will be described.

As best illustrated in FIGS. 1 through 4, the bed sore prevention assembly 10 generally includes a flexible panel 12 that has a first side 14, a second side 16, a top edge 18, a bottom edge 20, a first lateral edge 22 and a second lateral edge 24. The bottom edge 20 includes a pair of arcuate sections 26 that extend away from the top edge 18. The arcuate sections 26 are spaced from each other and from each of the first 22 and second 24 lateral edges. The arcuate sections 26 are positioned so that they may extend down the sides of a person when the panel 12 is positioned against the body of the person. Each of the lateral edges 22, 24 has a length generally between 6 inches and 14 inches. A distance from the top edge 18 to an outermost edge of the arcuate sections 26 is generally between 12 inches and 24 inches. The flexible panel 12 preferably includes a resiliently compressible material 28 that is covered with a cloth material 30. The resiliently compressible material 28 is preferably a foamed elastomeric material that has a thickness generally between ¼ inch and 2 inches.

A plurality of cushion members 31 is attached to the first side 14 of the panel 12. The cushion members 31 are each positioned generally between the top 18 and bottom 20 edges and are spaced from each other. Each of the cushion members 31 includes a resiliently compressible material 32 that is attached to the front side 14 and which is surrounded by a pocket 34 of cloth material. The resiliently compressible material 32 is again preferably a foamed elastomer. The cushion members 31 each have an oval shape such that each cushion member 31 includes a long axis and a short axis. The long axis of each of the cushion members 31 is orientated perpendicular to the top edge 18. The plurality of cushion members 31 includes a tailbone cushion 36 and a pair of hip cushions 38. The tailbone cushion 36 is positioned generally between the top 18 and bottom 20 edges and between the first 22 and second 24 side edges. The hip cushions 38 are each generally aligned with one of the arcuate sections 26. The hip cushions 38 are preferably spaced further from the top edge 18 than the tailbone cushion 36 by a distance of between 1 inch and 3 inches. The cloth of the pockets 34 and panel may be comprised of synthetic material, natural material or combinations thereof.

A fastening member selectively secures the panel 12 in a loop formation. The fastening member includes a first engaging member 40 that is attached to the first side 14 of the panel 12 and is positioned adjacent to the first lateral edge 22 and a second engaging member 42 that is attached to the second side 16 of the panel 12 and is positioned adjacent to the second lateral edge 24 of the panel 12. The first engaging member 40 is adapted for removably coupling with the second engaging member 42 to define a body wrap. The fastening member preferably comprises a hook and loop fastening means, though snaps or buttons may also be utilized.

Each of a pair of leg engaging members 50 is adapted for releasably securing the panel to one of a pair of legs of the person. Each of the leg engaging members 50 is attached to the bottom edge 20 and each of the leg engaging members 50 is positioned on one of the arcuate sections 26. The leg engaging members 50 each include an elongated strap 52 that has a first end 54 and a second end 56. A coupling assembly 58 is positioned on the strap 52 for selectively securing the strap 52 in a loop formation. A tether 60 is attached to an edge of the strap 52 between the first 54 and second 56 ends. The tether 60 preferably comprises a portion of cloth that is attached to one of the arcuate sections 26 such that a distance between the strap 52 and an associated one of the arcuate sections 26 is between 1 inch and 4 inches. The strap 52 may be extended about a leg of the person and removably secured thereto with the coupling assembly 58. The coupling assembly 58 preferably includes a hook and loop fasting means, though again snaps or buttons may be utilized.

In use, the panel 12 is wrapped about the body so that each of the hip cushions 38 abuts one of the hipbones of the person and the tailbone cushion 36 abuts the tailbone. The panel 12 is secured in place with the fastening member 40, 42. The straps 52 of the leg engaging members 50 are then each extended around and attached to one of the legs to aid the prevention of movement of the panel 12 on the person's body. When the person is bedridden for an extended period of time, the cushion members 31 protect those areas which are often susceptible to bed sores.

With respect to the above description then, it is to be realized that the optimum dimensional relationships for the parts of the invention, to include variations in size, materials, shape, form, function and manner of operation, assembly and use, are deemed readily apparent and obvious to one skilled in the art, and all equivalent relationships to those illustrated in the drawings and described in the specification are intended to be encompassed by the present invention.

Therefore, the foregoing is considered as illustrative only of the principles of the invention. Further, since numerous modifications and changes will readily occur to those skilled in the art, it is not desired to limit the invention to the exact construction and operation shown and described, and accordingly, all suitable modifications and equivalents may be resorted to, falling within the scope of the invention.

I claim:

1. A body protective device for preventing bedsores, the device being removably positioned around and abutting the pelvic area of a person, said device comprising:
   a flexible panel having a first side, a second side, a top edge, a bottom edge, a first lateral edge and a second lateral edge, said bottom edge including a pair of arcuate sections extending away from said top edge, said arcuate sections being spaced from each other and from each of said first and second lateral edges;
   a plurality of cushion members being attached to said first side of said panel, said cushion members being each positioned generally between said top and bottom edges, said cushion members being spaced from each other, said plurality of cushion members including a tailbone cushion and a pair of hip cushions, said tailbone cushion being positioned generally between said top and bottom edges and between said first and second lateral edges, said hip cushions each being generally aligned with one of said arcuate sections; and
   a fastening member for selectively securing said panel in a loop formation, said fastening member including a first engaging member attached to said first side of said panel and positioned adjacent to said first lateral edge and a second engaging member attached to said second side of said panel and positioned adjacent to said second lateral edge of said panel, wherein said first engaging member is adapted for removably coupling with said second engaging member to define a body wrap.

2. The device according to claim 1, further including a pair of leg engaging members each adapted for releasably securing said panel to one of a pair of legs of the person, each of said leg engaging members being attached to said bottom edge.

3. The device according to claim 1, wherein each of said lateral edges has a length generally between 6 inches and 14 inches, a distance from said top edge to an outermost edge of said arcuate sections being generally between 12 inches and 24 inches.

4. The device according to claim 1, wherein said flexible panel includes a resiliently compressible material covered with a cloth material.

5. The device according to claim 2, wherein each of said leg engaging members includes an elongated strap having a first end and a second end, a coupling assembly being positioned on said strap for selectively securing said strap in a loop formation, a tether being attached to an edge of said strap between said first and second ends, wherein said strap may be extended about a leg of the person and removably secured thereto.

6. The device according to claim 1, wherein each of said cushion members including a resiliently compressible material attached to said front side.

7. The device according to claim 1, wherein each of said cushion members has an oval shape such that each cushion member includes a long axis and a short axis, said long axis of each of said cushion members being orientated perpendicular to said top edge.

8. The device according to claim 5, said tether being attached to one of said arcuate sections such that a distance between said strap and an associated one of said arcuate sections is between 1 inch and 4 inches.

* * * * *